United States Patent
Loponen et al.

(10) Patent No.: US 10,820,599 B2
(45) Date of Patent: Nov. 3, 2020

(54) ENZYME EXHIBITING FRUCTAN HYDROLASE ACTIVITY

(71) Applicant: Oy Karl Fazer Ab, Helsinki (FI)

(72) Inventors: Jussi Loponen, Vantaa (FI); Markku Mikola, Lahti (FI); Juhani Sibakov, Espoo (FI)

(73) Assignee: Oy Karl Fazer Ab, Helsinki (FI)

( * ) Notice: Subject to any disclaimer, the term of this patent is extended or adjusted under 35 U.S.C. 154(b) by 0 days.

(21) Appl. No.: 16/899,611

(22) Filed: Jun. 12, 2020

(65) Prior Publication Data

US 2020/0296976 A1    Sep. 24, 2020

Related U.S. Application Data

(63) Continuation of application No. 16/309,480, filed as application No. PCT/FI2017/050469 on Jun. 22, 2017, now Pat. No. 10,716,308.

(30) Foreign Application Priority Data

Jun. 23, 2016 (FI) ..................................... 20165526

(51) Int. Cl.
| | |
|---|---|
| A21D 8/04 | (2006.01) |
| A23L 5/20 | (2016.01) |
| A21D 10/00 | (2006.01) |
| A23L 7/104 | (2016.01) |
| C12N 9/24 | (2006.01) |
| C12N 9/10 | (2006.01) |
| C12N 9/26 | (2006.01) |
| C12N 9/42 | (2006.01) |
| C12N 15/63 | (2006.01) |
| C12N 15/70 | (2006.01) |
| C12N 15/81 | (2006.01) |

(52) U.S. Cl.
CPC ........... *A21D 8/042* (2013.01); *A21D 10/005* (2013.01); *A23L 5/20* (2016.08); *A23L 5/25* (2016.08); *A23L 7/107* (2016.08); *C12N 9/1051* (2013.01); *C12N 9/2405* (2013.01); *C12N 9/2431* (2013.01); *C12N 9/2445* (2013.01); *C12N 15/63* (2013.01); *C12N 15/70* (2013.01); *C12N 15/815* (2013.01); *C12Y 302/01064* (2013.01); *C12Y 302/01065* (2013.01); *C12Y 204/01009* (2013.01); *C12Y 204/01243* (2013.01); *C12Y 302/01021* (2013.01); *C12Y 302/01022* (2013.01); *C12Y 302/01026* (2013.01); *C12Y 302/01153* (2013.01); *C12Y 302/01154* (2013.01)

(58) Field of Classification Search
CPC .... A21D 8/042; A21D 10/005; C12N 9/2431; C12N 15/63; C12N 9/1051; C12N 15/815; C12N 9/2445; C12N 15/70; C12N 9/2405; A23L 5/20; A23L 5/25; A23L 7/107; C12Y 302/01065; C12Y 302/01064; C12Y 302/01021; C12Y 204/01243; C12Y 204/01009; C12Y 302/01153; C12Y 302/01154; C12Y 302/01022; C12Y 302/01026
See application file for complete search history.

(56) References Cited

U.S. PATENT DOCUMENTS 8,460,911 B2   6/2013  Wyrobnik et al.
2011/0129572 A1   6/2011  Meier et al.

FOREIGN PATENT DOCUMENTS

| EP | 1084624 A2 | 3/2001 |
| WO | WO2009112464 A1 | 9/2009 |
| WO | WO2010097416 A1 | 9/2010 |

OTHER PUBLICATIONS

Abdelmaksoud et al: Comparison of Lactobacillus crispatus isolates from Lactobacillus-dominated vaginal microbiomes with isolates from microbiomes containing bacterial vaginosis-associated bacteria, Journal of General Microbiology, Mar. 1, 2016. vol. 162, No. 3, pp. 466-475.
Anderson et al: Content and molecular-weight distribution of dietary fiber compnents in whole-grain rye flour and bread. Journal of Agricultural and Food Chemistry, 2009, vol. 57, No. 5, pp. 2004-2008.
Database Genbank: Glycosyl hydrolase family 32. Lactobacillus amylovorus. May 27, 2013.
Database Genbank: Glycosyl hydrolase family 32. Lactobacillus crispatus. Jan. 27, 2016.
Goh et al: Functional analysis of the fructooligosaccharide utilization operon in lactobacillus paracasei 1195. Applied and Environmental Microbiology, 2007, vol. 73, No. 18, pp. 5716-5724.
Gänzle et al: Metabolism of Oligosaccharides and Starch in Lactobacilli: A Review Frontiers in Microbiology, Jan. 1, 2012, vol. 3.
Kant et al: Fructan hydrolase [Lactobacillus amylovorus GRL 1112]. GenBank accession No. ADQ59657. Jan. 30, 2014.
Kant et al: Genome Sequence of Lactobacillus amylovorus GRL1112, Journal of Bacteriology, Dec. 3, 2010. vol. 193, No. 3, pp. 789-790.

(Continued)

*Primary Examiner* — Delia M Ramirez
(74) *Attorney, Agent, or Firm* — Laine IP Oy; Mark W. Scott

(57) ABSTRACT

The present invention is related to an enzyme that allows efficient removal of fructan from grain and vegetable raw material. The enzyme according to the invention produces grain and vegetable material having a fructan content significantly lower compared to that of the starting material.

13 Claims, 6 Drawing Sheets

Specification includes a Sequence Listing.

(56) References Cited

OTHER PUBLICATIONS

Kant et al: Lactobacillus amylovorus GRL 1112, complete genome. GenBank accession No. CP002338, Jan. 30, 2014.
Kieronczyk et al: Ann. Anim. Sci. vol. 16, No. 3, pp. 653-678, 2016. Avian Crop Function—A Review.
Mitreva et al: GenBank accession No. KXI20556, Feb. 18, 2016. glycosyl hydrolase family 25 [Lactobacillus crispatus].
Müller et al: Fermentation of fructans by epiphytic lactic acid bacteria. Journal of Applied Bacteriology, 1994, vol. 76, No. 4, pp. 406-411.
Müller et al: Purification and substrate specificity of an extracellular fructanhydrolase from *Lactobacillus paracasei* ssp. *paracasei* p. 4134. New Phytologist, 1997, vol. 136, pp. 89-96.
Paludan-Müller et al: Purification and characterisation of an extracellular fructan β-fructosidase from a lactobacillus pentosus strain isolate from fermented fish. Systematic and Applied Microbiology, 2002, vol. 25, pp. 13-20.
Rakha et al: Characterisation of dietary fibre components in rye products. Food Chemistry 2010, vol. 119, No. 3, pp. 859-867.

SEQUENCE LISTING

```
<160> NUMBER OF SEQ ID NOS: 2

<210> SEQ ID NO 1
<211> LENGTH: 3936
<212> TYPE: DNA
<213> ORGANISM: Lactobacillus
<220> FEATURE:
<221> NAME/KEY: CDS
<222> LOCATION: 1..3936
<223> OTHER INFORMATION: /transl_table=11

<400> SEQUENCE: 1 atg agt cat aaa ttt aat aat tac ggt tta gta aca tcc ttt gct gca      48
Met Ser His Lys Phe Asn Asn Tyr Gly Leu Val Thr Ser Phe Ala Ala
1               5                  10                  15 gca aca ttg ctc agc tta tgt tta aca tca aat agt aat gtt aaa gca      96
Ala Thr Leu Leu Ser Leu Cys Leu Thr Ser Asn Ser Asn Val Lys Ala
                20                  25                  30 gat acg cag tcg cca gtt aat att gag caa aaa aat aaa tct gct gaa     144
Asp Thr Gln Ser Pro Val Asn Ile Glu Gln Lys Asn Lys Ser Ala Glu
            35                  40                  45 tta atc aag cag aat tct gac att tcc acc agc gca caa caa cac aac     192
Leu Ile Lys Gln Asn Ser Asp Ile Ser Thr Ser Ala Gln Gln His Asn
        50                  55                  60 aaa aat gct aat ggg aaa act gaa gat acg tct act caa tct aca tca     240
Lys Asn Ala Asn Gly Lys Thr Glu Asp Thr Ser Thr Gln Ser Thr Ser
65                  70                  75                  80 aca gac tta caa aat act aat gga aaa act gaa gat acg tct act caa     288
Thr Asp Leu Gln Asn Thr Asn Gly Lys Thr Glu Asp Thr Ser Thr Gln
                85                  90                  95 tct aca tca aca gac tta caa aat act aat acg caa aaa agc ttc aag     336
Ser Thr Ser Thr Asp Leu Gln Asn Thr Asn Thr Gln Lys Ser Phe Lys
            100                 105                 110 aat caa tca caa gaa cca gaa tct tcc act aaa gcc gga gaa gta aag     384
Asn Gln Ser Gln Glu Pro Glu Ser Ser Thr Lys Ala Gly Glu Val Lys
        115                 120                 125 aca tta aag gac ttt act ttc tca caa aac ggt aag tgg tct gaa caa     432
Thr Leu Lys Asp Phe Thr Phe Ser Gln Asn Gly Lys Trp Ser Glu Gln
130                 135                 140 aaa gat ggc att cat agt gat gcc aga ggt caa ggt gac agc ttt gca     480
Lys Asp Gly Ile His Ser Asp Ala Arg Gly Gln Gly Asp Ser Phe Ala
145                 150                 155                 160 tat act aag gtt aag gga gat aac ttt atg tat tct gca gat gtc gtc     528
Tyr Thr Lys Val Lys Gly Asp Asn Phe Met Tyr Ser Ala Asp Val Val
```

-continued

|     |     |     | 165 |     |     |     | 170 |     |     |     | 175 |     |     |     |      |
| --- | --- | --- | --- | --- | --- | --- | --- | --- | --- | --- | --- | --- | --- | --- | ---- |
| ttc | caa | act | aat | caa | ggt | gcc | gct | gca | ata | act | ttc | agg | gat | aat | aat  | 576
| Phe | Gln | Thr | Asn | Gln | Gly | Ala | Ala | Ala | Ile | Thr | Phe | Arg | Asp | Asn | Asn  |
|     |     |     | 180 |     |     |     | 185 |     |     |     | 190 |     |     |     |      |

```
ttc caa act aat caa ggt gcc gct gca ata act ttc agg gat aat aat        576
Phe Gln Thr Asn Gln Gly Ala Ala Ala Ile Thr Phe Arg Asp Asn Asn
            180             185             190 gat cct gat aat aaa gat ggt tat gct gta aat gtt gat gcc tct agc        624
Asp Pro Asp Asn Lys Asp Gly Tyr Ala Val Asn Val Asp Ala Ser Ser
        195             200             205 cat aag gct aaa ttc tgg cgc tgg cat gac aat aag gat tat caa tta        672
His Lys Ala Lys Phe Trp Arg Trp His Asp Asn Lys Asp Tyr Gln Leu
        210             215             220 atc gat gaa cgt gat gtt aag caa act gct gac aac act tat aac tta        720
Ile Asp Glu Arg Asp Val Lys Gln Thr Ala Asp Asn Thr Tyr Asn Leu
225             230             235             240 aaa gtc gtt gct aat ggt cat tgg ctt gaa tac ttt gtt aat gat gtt        768
Lys Val Val Ala Asn Gly His Trp Leu Glu Tyr Phe Val Asn Asp Val
                245             250             255 tta gtg gca agt aat ggt gat tat act ctt caa aag ggt gat aaa ggt        816
Leu Val Ala Ser Asn Gly Asp Tyr Thr Leu Gln Lys Gly Asp Lys Gly
            260             265             270 cag cct tca gta aca aac aat ggc tac ttt ggt tta ctc aat tgg aac        864
Gln Pro Ser Val Thr Asn Asn Gly Tyr Phe Gly Leu Leu Asn Trp Asn
        275             280             285 agt aat gtc att ttt aag aat gtt aaa tat aca aag ctt gat caa tca        912
Ser Asn Val Ile Phe Lys Asn Val Lys Tyr Thr Lys Leu Asp Gln Ser
        290             295             300 ttt act cct tta gta tcg gat atc act gtt act tca gat aag ggt aag        960
Phe Thr Pro Leu Val Ser Asp Ile Thr Val Thr Ser Asp Lys Gly Lys
305             310             315             320 gtt gag gag aaa ggt cag ttt tca cct gaa caa cca att tat att cag       1008
Val Glu Glu Lys Gly Gln Phe Ser Pro Glu Gln Pro Ile Tyr Ile Gln
                325             330             335 tac gta gat aac gat gct tca act gtt aat ttg aag gtt aag act gat       1056
Tyr Val Asp Asn Asp Ala Ser Thr Val Asn Leu Lys Val Lys Thr Asp
            340             345             350 tct cct aag gct aaa gta gtt gct tat gat ctt aat aat aat gca tac       1104
Ser Pro Lys Ala Lys Val Val Ala Tyr Asp Leu Asn Asn Asn Ala Tyr
        355             360             365 act gat tta aag aat att cca gtt cag gtt gga gca aat tac tta aca       1152
Thr Asp Leu Lys Asn Ile Pro Val Gln Val Gly Ala Asn Tyr Leu Thr
        370             375             380 gtg gtc agt gaa gta act gct tca gat ggt act aag gtt gaa tct gtc       1200
Val Val Ser Glu Val Thr Ala Ser Asp Gly Thr Lys Val Glu Ser Val
385             390             395             400 tac cgg att aat gtt cac cgt ctt cat cca aat gaa aat tat tat aat       1248
Tyr Arg Ile Asn Val His Arg Leu His Pro Asn Glu Asn Tyr Tyr Asn
                405             410             415 gaa ctt tat cgt gat caa tac cat ttt tca gtt aaa gag ggc tgg agc       1296
Glu Leu Tyr Arg Asp Gln Tyr His Phe Ser Val Lys Glu Gly Trp Ser
            420             425             430 aat gat cca aac ggt tta gtt tac ttt aat ggt aag tat cat atg ttc       1344
Asn Asp Pro Asn Gly Leu Val Tyr Phe Asn Gly Lys Tyr His Met Phe
        435             440             445 tat caa ttc tac gat gat act att tgg ggt cca atg cac tgg gca cac       1392
Tyr Gln Phe Tyr Asp Asp Thr Ile Trp Gly Pro Met His Trp Ala His
        450             455             460 gct aca agt aaa gat cta atc cat tgg aag aat gaa cca att gct ttg       1440
Ala Thr Ser Lys Asp Leu Ile His Trp Lys Asn Glu Pro Ile Ala Leu
465             470             475             480 tat cct gat gca aat ggt gca atg ttc tca ggt tca atc gtt gtt gat       1488
```

```
                    Tyr Pro Asp Ala Asn Gly Ala Met Phe Ser Gly Ser Ile Val Val Asp
                                        485                 490                 495 aag gga aac act tct ggc ttg ttt gac aat gat aaa ggt gga ctt gtt            1536
Lys Gly Asn Thr Ser Gly Leu Phe Asp Asn Asp Lys Gly Gly Leu Val
            500                 505                 510 gcc tta gtc act acc gat ggt aat ggt caa aga att gaa ctt gct tac            1584
Ala Leu Val Thr Thr Asp Gly Asn Gly Gln Arg Ile Glu Leu Ala Tyr
                515                 520                 525 agt aga gat gaa ggt aag act tgg gac aaa ctt cct aat tta gta gct            1632
Ser Arg Asp Glu Gly Lys Thr Trp Asp Lys Leu Pro Asn Leu Val Ala
        530                 535                 540 gat tgg caa aaa gat cca tta caa gtc caa gat ttc cgt gat cca aaa            1680
Asp Trp Gln Lys Asp Pro Leu Gln Val Gln Asp Phe Arg Asp Pro Lys
545                 550                 555                 560 gtc ttc cgc tgg aat gat aaa tgg ttc atg gta ctt gct ggt ggt cca            1728
Val Phe Arg Trp Asn Asp Lys Trp Phe Met Val Leu Ala Gly Gly Pro
                565                 570                 575 cta aga att tat tca tca aca aat tta caa aat tgg caa gtt gaa tct            1776
Leu Arg Ile Tyr Ser Ser Thr Asn Leu Gln Asn Trp Gln Val Glu Ser
                580                 585                 590 gaa tat tca aat att aac act gaa tgt cca gat ctt tat cca ata aga            1824
Glu Tyr Ser Asn Ile Asn Thr Glu Cys Pro Asp Leu Tyr Pro Ile Arg
        595                 600                 605 gca aat gat ggc caa ctt aag tgg gtt cta tca cgt ggc gga cgt ttc            1872
Ala Asn Asp Gly Gln Leu Lys Trp Val Leu Ser Arg Gly Gly Arg Phe
610                 615                 620 tac aag att ggt gat ttt aag gaa gtt aat ggc aag tgg agt ttt att            1920
Tyr Lys Ile Gly Asp Phe Lys Glu Val Asn Gly Lys Trp Ser Phe Ile
625                 630                 635                 640 cca gat gaa gct tat aaa gat caa gac ggc att atg aat ttt ggt aaa            1968
Pro Asp Glu Ala Tyr Lys Asp Gln Asp Gly Ile Met Asn Phe Gly Lys
                645                 650                 655 gat tct tat gct gca atg act tac tac caa cac agt ttt ggc acg gaa            2016
Asp Ser Tyr Ala Ala Met Thr Tyr Tyr Gln His Ser Phe Gly Thr Glu
            660                 665                 670 aaa gat cca act tta cct gat att atc gaa gaa aat tgg atg aac aat            2064
Lys Asp Pro Thr Leu Pro Asp Ile Ile Glu Glu Asn Trp Met Asn Asn
                675                 680                 685 tgg gat tat tgt aac ctt gtc ggt aat act gtt ggt caa agt ttt aac            2112
Trp Asp Tyr Cys Asn Leu Val Gly Asn Thr Val Gly Gln Ser Phe Asn
        690                 695                 700 gga aca tat aac ctt aac tta aaa gtt ggt tta gtc aaa gat ggg gac            2160
Gly Thr Tyr Asn Leu Asn Leu Lys Val Gly Leu Val Lys Asp Gly Asp
705                 710                 715                 720 aaa tat ctt cta act caa aca cca att aaa gcc tat gaa gct tta cga            2208
Lys Tyr Leu Leu Thr Gln Thr Pro Ile Lys Ala Tyr Glu Ala Leu Arg
                725                 730                 735 gat aat gct cac aaa gtt gaa tat aaa gat gtt act gta aca cca aat            2256
Asp Asn Ala His Lys Val Glu Tyr Lys Asp Val Thr Val Thr Pro Asn
            740                 745                 750 aac gac tta ttt aag aac ttt aaa ggc gat tca tac gaa att gtt tct            2304
Asn Asp Leu Phe Lys Asn Phe Lys Gly Asp Ser Tyr Glu Ile Val Ser
                755                 760                 765 acc ttt aga cca tct aaa tct act act aaa gtt ggc ttt aat gtt cgt            2352
Thr Phe Arg Pro Ser Lys Ser Thr Thr Lys Val Gly Phe Asn Val Arg
        770                 775                 780 gta ggt aaa ggt caa gct aca aaa gtt att tat gat tta acc aca aat            2400
Val Gly Lys Gly Gln Ala Thr Lys Val Ile Tyr Asp Leu Thr Thr Asn
785                 790                 795                 800
```

```
aag atc tat att gac cgt agt aaa tca gga gtt caa att aac aat aaa    2448
Lys Ile Tyr Ile Asp Arg Ser Lys Ser Gly Val Gln Ile Asn Asn Lys
            805                 810                 815 ttt agt gag ctt aat gaa caa cca gtt act cgc aat gca gat ggc agt    2496
Phe Ser Glu Leu Asn Glu Gln Pro Val Thr Arg Asn Ala Asp Gly Ser
        820                 825                 830 atc agc tta cat tta tat gtt gac cgt gct agt gtc gaa gca ttt act    2544
Ile Ser Leu His Leu Tyr Val Asp Arg Ala Ser Val Glu Ala Phe Thr
    835                 840                 845 aaa ggt gat acg gta ctt ggt gca aat caa att ttt cca gca cct caa    2592
Lys Gly Asp Thr Val Leu Gly Ala Asn Gln Ile Phe Pro Ala Pro Gln
850                 855                 860 agt tta ggc ttg caa gtt gtt tct gaa ggt gga gat tct aaa gct gat    2640
Ser Leu Gly Leu Gln Val Val Ser Glu Gly Gly Asp Ser Lys Ala Asp
            865                 870                 875                 880 att act ctt tac cca ata aag agc gtt tgg aca gat aag caa aaa gta    2688
Ile Thr Leu Tyr Pro Ile Lys Ser Val Trp Thr Asp Lys Gln Lys Val
        885                 890                 895 aat aaa cct tta gaa att gtc caa gtt tca cca aaa gaa gtt cgc tta    2736
Asn Lys Pro Leu Glu Ile Val Gln Val Ser Pro Lys Glu Val Arg Leu
    900                 905                 910 aac gtt ggt gat tca act aca tta act gct tat gtc atg cct ggc aat    2784
Asn Val Gly Asp Ser Thr Thr Leu Thr Ala Tyr Val Met Pro Gly Asn
915                 920                 925 gtt tct caa gcc cta gat tgg tca att aat gat gaa agt ttg gca agt    2832
Val Ser Gln Ala Leu Asp Trp Ser Ile Asn Asp Glu Ser Leu Ala Ser
            930                 935                 940 atc aca aaa gat cca gaa tca aat tca tta aag att gtt gcc aag aaa    2880
Ile Thr Lys Asp Pro Glu Ser Asn Ser Leu Lys Ile Val Ala Lys Lys
945                 950                 955                 960 gct gga act ttg act gtt aca gtt aaa tca cat gaa gat cct tct tta    2928
Ala Gly Thr Leu Thr Val Thr Val Lys Ser His Glu Asp Pro Ser Leu
            965                 970                 975 tct aag aca tat aaa att aca att tta aag aat aac ttt aag act aat    2976
Ser Lys Thr Tyr Lys Ile Thr Ile Leu Lys Asn Asn Phe Lys Thr Asn
        980                 985                 990 att aaa gac ttg aag cca tta tct gga aat tgg tat gta gat gat caa    3024
Ile Lys Asp Leu Lys Pro Leu Ser Gly Asn Trp Tyr Val Asp Asp Gln
    995                 1000                1005 gac tta cac gat gaa aat gtc agt tca aat gac tac att atg agt cca    3072
Asp Leu His Asp Glu Asn Val Ser Ser Asn Asp Tyr Ile Met Ser Pro
1010                1015                1020 act aag gtt tca tca tca gaa tat gat atg aat ctt gac gtc aaa tac    3120
Thr Lys Val Ser Ser Ser Glu Tyr Asp Met Asn Leu Asp Val Lys Tyr
1025                1030                1035                1040 caa aaa ggt tta gta aac atc ttc ttt gca tca gcc aat gaa gat cca    3168
Gln Lys Gly Leu Val Asn Ile Phe Phe Ala Ser Ala Asn Glu Asp Pro
            1045                1050                1055 aat ggt gca tat tca ctc caa ctt ggt ggt gat aag acc tta cgt ctc    3216
Asn Gly Ala Tyr Ser Leu Gln Leu Gly Gly Asp Lys Thr Leu Arg Leu
        1060                1065                1070 ttc cgt ttc tat gga gat aca att act act acc gat tta cca gct gct    3264
Phe Arg Phe Tyr Gly Asp Thr Ile Thr Thr Thr Asp Leu Pro Ala Ala
    1075                1080                1085 tta aat gat ggc aaa ctt cac cat gtc gca att cat aag aca caa aat    3312
Leu Asn Asp Gly Lys Leu His His Val Ala Ile His Lys Thr Gln Asn
1090                1095                1100 gcc gtt aag gtt acg att gat ggt aaa gag gca atg gat tat acc ttt    3360
Ala Val Lys Val Thr Ile Asp Gly Lys Glu Ala Met Asp Tyr Thr Phe
1105                1110                1115                1120
```

```
gat aaa gtt gat cct ggc ttt aat agt gcc tat gtt ggt tta ggt tta      3408
Asp Lys Val Asp Pro Gly Phe Asn Ser Ala Tyr Val Gly Leu Gly Leu
        1125                1130                1135 tgg gat ggt gct gct gat ttc cag aac tta tac gtc aaa gca gca aca      3456
Trp Asp Gly Ala Ala Asp Phe Gln Asn Leu Tyr Val Lys Ala Ala Thr
        1140                1145                1150 gaa aat gac gat aat tct tca tca tca atc gac ttt aat gat caa gaa      3504
Glu Asn Asp Asp Asn Ser Ser Ser Ser Ile Asp Phe Asn Asp Gln Glu
        1155                1160                1165 ata cct aat gtt tca act gat gac aat aat tcg att atc gag aaa cca      3552
Ile Pro Asn Val Ser Thr Asp Asp Asn Asn Ser Ile Ile Glu Lys Pro
        1170                1175                1180 agt gaa act gtt aaa aca gtt gtc ttt acg gca aag tct tta atg cat      3600
Ser Glu Thr Val Lys Thr Val Val Phe Thr Ala Lys Ser Leu Met His
1185            1190                1195                1200 aac gca ttt gtt tac gat aac caa ggt aag cga att gaa aaa att gtt      3648
Asn Ala Phe Val Tyr Asp Asn Gln Gly Lys Arg Ile Glu Lys Ile Val
                1205                1210                1215 ttg aag gct ggg tcc gtc tta aag gtc ggt cat ata aaa ctc atc aat      3696
Leu Lys Ala Gly Ser Val Leu Lys Val Gly His Ile Lys Leu Ile Asn
        1220                1225                1230 cat aag aga tac tac caa tta gat aat ggt aaa tat att aag gcc ggt      3744
His Lys Arg Tyr Tyr Gln Leu Asp Asn Gly Lys Tyr Ile Lys Ala Gly
        1235                1240                1245 aac att gat gcg tat gtc aga aaa tta cgt aga aat gcc ttt gtt tac      3792
Asn Ile Asp Ala Tyr Val Arg Lys Leu Arg Arg Asn Ala Phe Val Tyr
1250                1255                1260 aat cgt gct ggt aag cat att aaa aag agt ctg atc aga aaa ggt aag      3840
Asn Arg Ala Gly Lys His Ile Lys Lys Ser Leu Ile Arg Lys Gly Lys
1265            1270                1275                1280 aaa gtt aaa acc tat ggt tca cca gtt gta atc aaa ggt ata aaa tat      3888
Lys Val Lys Thr Tyr Gly Ser Pro Val Val Ile Lys Gly Ile Lys Tyr
                1285                1290                1295 tac att gtt ggt aat aac aga tat att aaa gcg gtt aac ttt atg taa      3936
Tyr Ile Val Gly Asn Asn Arg Tyr Ile Lys Ala Val Asn Phe Met
        1300                1305                1310
```

<210> SEQ ID NO 2
<211> LENGTH: 1311
<212> TYPE: PRT
<213> ORGANISM: Lactobacillus
<220> FEATURE:
<223> OTHER INFORMATION: [CDS]:1..3936 from SEQ ID NO 1

<400> SEQUENCE: 2

```
Met Ser His Lys Phe Asn Asn Tyr Gly Leu Val Thr Ser Phe Ala Ala
1               5                   10                  15

Ala Thr Leu Leu Ser Leu Cys Leu Thr Ser Asn Ser Asn Val Lys Ala
                20                  25                  30

Asp Thr Gln Ser Pro Val Asn Ile Glu Gln Lys Asn Lys Ser Ala Glu
            35                  40                  45

Leu Ile Lys Gln Asn Ser Asp Ile Ser Thr Ser Ala Gln Gln His Asn
        50                  55                  60

Lys Asn Ala Asn Gly Lys Thr Glu Asp Thr Ser Thr Gln Ser Thr Ser
65                  70                  75                  80

Thr Asp Leu Gln Asn Thr Asn Gly Lys Thr Glu Asp Thr Ser Thr Gln
                85                  90                  95

Ser Thr Ser Thr Asp Leu Gln Asn Thr Asn Thr Gln Lys Ser Phe Lys
            100                 105                 110
```

```
Asn Gln Ser Gln Glu Pro Ser Ser Thr Lys Ala Gly Glu Val Lys
        115                 120                 125

Thr Leu Lys Asp Phe Thr Phe Ser Gln Asn Gly Lys Trp Ser Glu Gln
130                 135                 140

Lys Asp Gly Ile His Ser Asp Ala Arg Gly Gln Gly Asp Ser Phe Ala
145                 150                 155                 160

Tyr Thr Lys Val Lys Gly Asp Asn Phe Met Tyr Ser Ala Asp Val Val
                165                 170                 175

Phe Gln Thr Asn Gln Gly Ala Ala Ile Thr Phe Arg Asp Asn Asn
            180                 185                 190

Asp Pro Asp Asn Lys Asp Gly Tyr Ala Val Asn Val Asp Ala Ser Ser
            195                 200                 205

His Lys Ala Lys Phe Trp Arg Trp His Asp Asn Lys Asp Tyr Gln Leu
        210                 215                 220

Ile Asp Glu Arg Asp Val Lys Gln Thr Ala Asp Asn Thr Tyr Asn Leu
225                 230                 235                 240

Lys Val Val Ala Asn Gly His Trp Leu Glu Tyr Phe Val Asn Asp Val
                245                 250                 255

Leu Val Ala Ser Asn Gly Asp Tyr Thr Leu Gln Lys Gly Asp Lys Gly
            260                 265                 270

Gln Pro Ser Val Thr Asn Asn Gly Tyr Phe Gly Leu Leu Asn Trp Asn
        275                 280                 285

Ser Asn Val Ile Phe Lys Asn Val Lys Tyr Thr Lys Leu Asp Gln Ser
        290                 295                 300

Phe Thr Pro Leu Val Ser Asp Ile Thr Val Thr Ser Asp Lys Gly Lys
305                 310                 315                 320

Val Glu Glu Lys Gly Gln Phe Ser Pro Glu Gln Pro Ile Tyr Ile Gln
                325                 330                 335

Tyr Val Asp Asn Asp Ala Ser Thr Val Asn Leu Lys Val Lys Thr Asp
            340                 345                 350

Ser Pro Lys Ala Lys Val Val Ala Tyr Asp Leu Asn Asn Asn Ala Tyr
        355                 360                 365

Thr Asp Leu Lys Asn Ile Pro Val Gln Val Gly Ala Asn Tyr Leu Thr
370                 375                 380

Val Val Ser Glu Val Thr Ala Ser Asp Gly Thr Lys Val Glu Ser Val
385                 390                 395                 400

Tyr Arg Ile Asn Val His Arg Leu His Pro Asn Glu Asn Tyr Tyr Asn
                405                 410                 415

Glu Leu Tyr Arg Asp Gln Tyr His Phe Ser Val Lys Glu Gly Trp Ser
            420                 425                 430

Asn Asp Pro Asn Gly Leu Val Tyr Phe Asn Gly Lys Tyr His Met Phe
            435                 440                 445

Tyr Gln Phe Tyr Asp Asp Thr Ile Trp Gly Pro Met His Trp Ala His
        450                 455                 460

Ala Thr Ser Lys Asp Leu Ile His Trp Lys Asn Glu Pro Ile Ala Leu
465                 470                 475                 480

Tyr Pro Asp Ala Asn Gly Ala Met Phe Ser Gly Ser Ile Val Val Asp
                485                 490                 495

Lys Gly Asn Thr Ser Gly Leu Phe Asp Asn Asp Lys Gly Gly Leu Val
            500                 505                 510

Ala Leu Val Thr Thr Asp Gly Asn Gly Gln Arg Ile Glu Leu Ala Tyr
        515                 520                 525
```

```
Ser Arg Asp Glu Gly Lys Thr Trp Asp Lys Leu Pro Asn Leu Val Ala
530                 535                 540

Asp Trp Gln Lys Asp Pro Leu Gln Val Gln Asp Phe Arg Asp Pro Lys
545                 550                 555                 560

Val Phe Arg Trp Asn Asp Lys Trp Phe Met Val Leu Ala Gly Gly Pro
                565                 570                 575

Leu Arg Ile Tyr Ser Ser Thr Asn Leu Gln Asn Trp Gln Val Glu Ser
            580                 585                 590

Glu Tyr Ser Asn Ile Asn Thr Glu Cys Pro Asp Leu Tyr Pro Ile Arg
        595                 600                 605

Ala Asn Asp Gly Gln Leu Lys Trp Val Leu Ser Arg Gly Gly Arg Phe
610                 615                 620

Tyr Lys Ile Gly Asp Phe Lys Glu Val Asn Gly Lys Trp Ser Phe Ile
625                 630                 635                 640

Pro Asp Glu Ala Tyr Lys Asp Gln Asp Gly Ile Met Asn Phe Gly Lys
                645                 650                 655

Asp Ser Tyr Ala Ala Met Thr Tyr Tyr Gln His Ser Phe Gly Thr Glu
            660                 665                 670

Lys Asp Pro Thr Leu Pro Asp Ile Ile Glu Glu Asn Trp Met Asn Asn
        675                 680                 685

Trp Asp Tyr Cys Asn Leu Val Gly Asn Thr Val Gly Gln Ser Phe Asn
690                 695                 700

Gly Thr Tyr Asn Leu Asn Leu Lys Val Gly Leu Val Lys Asp Gly Asp
705                 710                 715                 720

Lys Tyr Leu Leu Thr Gln Thr Pro Ile Lys Ala Tyr Glu Ala Leu Arg
                725                 730                 735

Asp Asn Ala His Lys Val Glu Tyr Lys Asp Val Thr Val Thr Pro Asn
            740                 745                 750

Asn Asp Leu Phe Lys Asn Phe Lys Gly Asp Ser Tyr Glu Ile Val Ser
        755                 760                 765

Thr Phe Arg Pro Ser Lys Ser Thr Thr Lys Val Gly Phe Asn Val Arg
770                 775                 780

Val Gly Lys Gly Gln Ala Thr Lys Val Ile Tyr Asp Leu Thr Thr Asn
785                 790                 795                 800

Lys Ile Tyr Ile Asp Arg Ser Lys Ser Gly Val Gln Ile Asn Asn Lys
                805                 810                 815

Phe Ser Glu Leu Asn Glu Gln Pro Val Thr Arg Asn Ala Asp Gly Ser
            820                 825                 830

Ile Ser Leu His Leu Tyr Val Asp Arg Ala Ser Val Glu Ala Phe Thr
        835                 840                 845

Lys Gly Asp Thr Val Leu Gly Ala Asn Gln Ile Phe Pro Ala Pro Gln
850                 855                 860

Ser Leu Gly Leu Gln Val Val Ser Glu Gly Gly Asp Ser Lys Ala Asp
865                 870                 875                 880

Ile Thr Leu Tyr Pro Ile Lys Ser Val Trp Thr Asp Lys Gln Lys Val
                885                 890                 895

Asn Lys Pro Leu Glu Ile Val Gln Val Ser Pro Lys Glu Val Arg Leu
            900                 905                 910

Asn Val Gly Asp Ser Thr Thr Leu Thr Ala Tyr Val Met Pro Gly Asn
        915                 920                 925

Val Ser Gln Ala Leu Asp Trp Ser Ile Asn Asp Glu Ser Leu Ala Ser
930                 935                 940

Ile Thr Lys Asp Pro Glu Ser Asn Ser Leu Lys Ile Val Ala Lys Lys
```

```
                    945             950              955                960
       Ala Gly Thr Leu Thr Val Thr Val Lys Ser His Glu Asp Pro Ser Leu
                           965             970                 975

Ser Lys Thr Tyr Lys Ile Thr Ile Leu Lys Asn Asn Phe Lys Thr Asn
                           980             985                 990

Ile Lys Asp Leu Lys Pro Leu Ser Gly Asn Trp Tyr Val Asp Asp Gln
                   995            1000                1005

Asp Leu His Asp Glu Asn Val Ser Ser Asn Asp Tyr Ile Met Ser Pro
                  1010            1015                1020

Thr Lys Val Ser Ser Ser Glu Tyr Asp Met Asn Leu Asp Val Lys Tyr
       1025                1030                1035                1040

Gln Lys Gly Leu Val Asn Ile Phe Phe Ala Ser Ala Asn Glu Asp Pro
                          1045             1050                1055

Asn Gly Ala Tyr Ser Leu Gln Leu Gly Gly Asp Lys Thr Leu Arg Leu
                          1060             1065                1070

Phe Arg Phe Tyr Gly Asp Thr Ile Thr Thr Thr Asp Leu Pro Ala Ala
                          1075             1080                1085

Leu Asn Asp Gly Lys Leu His His Val Ala Ile His Lys Thr Gln Asn
                  1090            1095                1100

Ala Val Lys Val Thr Ile Asp Gly Lys Glu Ala Met Asp Tyr Thr Phe
       1105                1110                1115                1120

Asp Lys Val Asp Pro Gly Phe Asn Ser Ala Tyr Val Gly Leu Gly Leu
                          1125             1130                1135

Trp Asp Gly Ala Ala Asp Phe Gln Asn Leu Tyr Val Lys Ala Ala Thr
                          1140             1145                1150

Glu Asn Asp Asp Asn Ser Ser Ser Ile Asp Phe Asn Asp Gln Glu
                          1155             1160                1165

Ile Pro Asn Val Ser Thr Asp Asp Asn Asn Ser Ile Ile Glu Lys Pro
                  1170            1175                1180

Ser Glu Thr Val Lys Thr Val Val Phe Thr Ala Lys Ser Leu Met His
       1185                1190                1195                1200

Asn Ala Phe Val Tyr Asp Asn Gln Gly Lys Arg Ile Glu Lys Ile Val
                          1205             1210                1215

Leu Lys Ala Gly Ser Val Leu Lys Val Gly His Ile Lys Leu Ile Asn
                          1220             1225                1230

His Lys Arg Tyr Tyr Gln Leu Asp Asn Gly Lys Tyr Ile Lys Ala Gly
                          1235             1240                1245

Asn Ile Asp Ala Tyr Val Arg Lys Leu Arg Arg Asn Ala Phe Val Tyr
                  1250            1255                1260

Asn Arg Ala Gly Lys His Ile Lys Lys Ser Leu Ile Arg Lys Gly Lys
       1265                1270                1275                1280

Lys Val Lys Thr Tyr Gly Ser Pro Val Val Ile Lys Gly Ile Lys Tyr
                          1285             1290                1295

Tyr Ile Val Gly Asn Asn Arg Tyr Ile Lys Ala Val Asn Phe Met
                          1300             1305                1310
```

ENZYME EXHIBITING FRUCTAN HYDROLASE ACTIVITY

This application is a continuation of U.S. application Ser. No. 16/309,480, filed Dec. 13, 2018, which is a U.S. National Stage Application of International Application No. PCT/FI2017/050469, filed Jun. 22, 2017, which claimed priority to Finnish Application No. 20165526, filed Jun. 23, 2016, the entirety of each of which is hereby incorporated by reference.

FIELD OF THE INVENTION

The present invention is directed to an enzyme that allows efficient removal of fructan from grain and vegetable raw material. The enzyme according to the invention produces grain and vegetable material having a fructan content significantly lower compared to that of the starting material. The low-fructan grain and vegetable materials can be used in producing low-fructan grain and vegetable ingredients, products suitable e.g. for low-FODMAP diet, and various cereal and vegetable food products with dietary benefits. The present invention is also directed to products containing low-fructan grain or vegetable ingredients and to products containing the enzyme, such as improvers and premixes for baking purposes.

BACKGROUND OF THE INVENTION

Digestion-related problems are a frequent cause of general and social discomfort. These problems cover a diverse selection of gastrointestinal symptoms of which bloating, gas production, abdominal pain, overall discomfort, constipation, and loose stools are among the most frequent. Today many of the sufferers of such symptoms are believed to suffer from irritable bowel syndrome (IBS). IBS is clearly more frequent in women and it is believed to concern 10-20% of Western population; i.e. IBS is more frequent in Western population than lactose-intolerance (many people having lactose intolerance, though, might have IBS and vice versa).

Currently there is no good medical cure for IBS. Much attention has been paid on dietary management of IBS. Most attention has been paid on a diet called LOW-FODMAP diet. The idea of the diet is to avoid food items that contain FODMAP compounds. Term FODMAP is derived from "Fermentable, Oligo-, Di-, Monosaccharides, and Polyols". FODMAPs are short chain carbohydrates and monosaccharides, which are poorly absorbed in the small intestine. FODMAP compounds include fructans (including FOS), galactans (especially GOS), and polyols. Also lactose and excess fructose can be considered as FODMAP compounds among people with impaired digestion or absorption of these compounds.

Common sources of fructans include for example wheat, rye, onion, Jerusalem artichoke, and garlic. Some examples of fructan contents of grains are as follows: rye (bran) 7% (on grain material basis), rye (grain) 3-7%, and wheat flour 1-4%. Although wheat is not generally considered as being especially rich in FODMAP compounds, its relatively high consumption makes it a relevant source of fructans. This is why the FODMAP diet guidelines instruct to avoid wheat. Rye consumption is high in Northern Europe. Rye bread contains more FODMAP compounds compared to wheat bread, because whole grain rye contains more fructans than wheat flour.

Fructans are built up of fructose residues, normally with a terminal sucrose unit (i.e. a glucose-fructose disaccharide). The linkage position of the fructose residues determines the type of the fructan. The basic types of single-linkage fructans are inulin and levan (or phlein). Additionally, there exists a mixed-linkage fructan called graminan.

Some prior art related to levels of fructan in bread is existing. In the article by Andersson et al. (2009) it was shown that the yeast fermented bread and especially the sourdough bread had lower contents of fructan as compared to whole grain rye flour. The results of Andersson et al. show that the fructan content of whole grain rye can be reduced from 5.0% to 1.9% by sourdough (62% reduction) and to 3.4% by yeast fermentation (32% reduction). The results also show that fructans are degraded during the bread-making process resulting in lower contents of total and extractable dietary fiber in the bread.

Article by Rakha et al. (2010) discloses that during bread making, the low-molecular weight fraction of fructan is most available for degradation by yeast or by endogenous enzymes present in the ingredients. According to Rakha et al., the fructan content in rye milling fractions ranges from 3.4% in inner endosperm to 5.0% in bran. The fructan content of rye breads varied from 1.9% to 4.0%, with an average of 2.8% in crisp breads, with a sample containing only whole grain rye flour being the highest in fructan content.

The dough according to US patent application US 2011/0129572 A1 comprises at least one fructose-containing polysaccharide and at least one enzyme capable of degrading said polysaccharide into short-chained fructo-oligosaccharide (FOS) and fructose. The baked product produced using this dough was said to have an increased softness compared to otherwise identical control bread or baked product produced using dough not containing the enzyme.

The discovery related to lowering the fructan amounts in plant material of patent application EP 1084624 A2 is that while *Lactobacillus* strains in general do not degrade fructan, there are *Lactobacillus* strains that do have this property. According to EP 1084624 A2, those strains are preferably *Lactobacillus paracasei* and *Lactobacillus plantarum*.

Müller et al (1994) studied fermentation of fructans by epiphytic lactic acid bacteria. Strains of epiphytic lactic acid bacteria were isolated from forage grasses and their ability to hydrolyze fructans was studied. Only 16 out of 712 strains utilized fructans. Said strains were identified as *Lactobacillus paracasei* subsp. *paracasei*, *Lactobacillus brevis* and *Pediococcus pentosaceus*.

As can be noted from above, some techniques to alter fructan levels are currently known and used. Additionally, it is known that sour bread has naturally lower levels of fructan. These fructan lowering techniques are generally based on using fermentation or specific fructan degrading enzymes.

Several fructan degrading enzymes are known in the art. Glycoside hydrolase family GH32 contains invertases and also enzymes that hydrolyze fructose containing polysaccharides such as inulinases, exo-inulinases, levanases and β-2,6-fructan 6-levanbiohydrolases, fructan β-(2,1)-fructosidase/1-exohydrolases or fructan β-(2,6)-fructosidase/6-exohydrolases, as well as enzymes displaying transglycosylating activities such as sucrose:sucrose 1-fructosyltransferases, fructan:fructan 1-fructosyltransferases, sucrose:fructan 6-fructosyltransferases, fructan:fructan 6G-fructosyltransferases and levan fructosyltransferases.

Extracellular enzymes such as inulinase that hydrolyze fructans are extracted for example from *Aspergillus niger* and are commercially available. These extracellular enzymes are naturally occurring enzymes that are isolated or extracted from their natural environments. However, these extracellular fructanase enzymes are expensive and difficult to obtain in sufficient amounts and high purity for large-scale applications.

For example, Paludan-Müller et al (2002) studied purification and characterization of an extracellular fructan β-fructosidase from a *Lactobacillus pentosus* strain isolated from fermented fish. An extracellular fructanhydrolase from *Lactobacillus paracasei* ssp. *paracasei* P 4134 was studied by Müller et al (1997), while Goh et al (2007) characterized a fructan hydrolase from *Lactobacillus paracasei* 1195. Document WO 2010/097416 A1 discloses a recombinant protein with fructanase activity comprising a fragment of a natural occurring protein derived from lactic acid bacteria such as *Lactobacillus*.

Moreover, with the use of known fructan-degrading enzymes, such as endo-fructanase, inulinase, or levanase, there is a possibility that fructo-oligosaccharides (FOS) are formed as degradation products as by this means not all fructan is converted to fructose. Therefore, there is still a need for a specific fructan degrading enzyme (fructanase, fructan hydrolase) that is able to decompose fructans efficiently without formation of FOS.

FOS are carbohydrates that the human body cannot fully digest and can thus function as prebiotics. There are some positive effects suggested for FOS. For example, they may produce substances that stop the growth of harmful, toxic gram-negative and positive bacteria in the intestines. However, according to the currently available scientific evidence FOS can execute some harmful effects. FOS can cause e.g. bloating, flatulence, abdominal and intestinal discomfort, and eructation. Furthermore, people with lactose intolerance were shown to particularly suffer from these side effects. The reason for these symptoms may be that FOS are generally gastrointestinally more active than fructan polymer, since the intestinal microflora ferments them more rapidly. Moreover, fructose can also considered being a FODMAP-compound with people having impaired fructose absorption. This is a problem when no comparable amount of glucose is present in the food item or meal. This is because fructose absorption in human body occurs along with glucose-induced uptake system. The excess fructose concentration (vs glucose concentration) is, however, easy to tackle with food recipe or meal formulations.

What is still needed in the art are grain and vegetable materials that are substantially free of fructans and FOS and thereby can be used to prepare products that are suitable for low-FODMAP diets. What is also still needed in the art is an efficient method and means for fructan removal from grain and vegetable material that would not result in unfavorable degradation products, especially FOS. Therefore, a method and means that would enable the efficient removal of fructan would be very beneficial for the development of food products suitable for low-FODMAP diet. Consumption of these food products would not cause gastrointestinal problems. Said food products could even have a positive effect on gastrointestinal health and in that way on general well-being.

SUMMARY OF THE INVENTION

The invention is defined by the features of the independent claims. Some specific embodiments are defined in the dependent claims.

The present invention is based on the finding that a novel enzyme isolated from a strain of *Lactobacillus* is capable to efficiently degrade and remove fructan of grain and vegetable materials.

According to a first aspect of the present invention there is provided a DNA construct comprising a nucleotide sequence encoding an extracellular fructanase, wherein said nucleotide sequence comprises the nucleotide sequence shown in SEQ ID No. 1 or a sequence analogous thereto having at least 96% identity to the nucleotide sequence shown in SEQ ID No. 1.

According to a second aspect of the present invention, there is provided an enzyme exhibiting fructan hydrolase activity which enzyme comprises a polypeptide having an amino acid sequence essentially as shown in SEQ ID. No. 2.

According to a further aspect of the present invention, there is provided a recombinant expression vector comprising the above mentioned DNA construct, as well as a cell comprising said recombinant expression vector.

According to a further aspect of the present invention, there is provided a method of producing an enzyme exhibiting fructan hydrolase activity, the method comprising culturing a cell as defined above under conditions permitting the production of the enzyme, and recovering the enzyme from the culture.

According to a further aspect of the present invention, there is provided an enzyme exhibiting fructan hydrolase activity, which enzyme is encoded by a DNA construct as defined above or is produced by the above defined method.

According to a further aspect of the present invention, there is provided an enzyme preparation for the degradation of fructan, said preparation comprising an enzyme according to the present invention.

According to a further aspect of the present invention, there is provided the use of an enzyme or an enzyme preparation according to the invention for the degradation of fructan in grain materials or in vegetables.

According to a further aspect of the present invention, there is provided the use of an enzyme or an enzyme preparation according to the invention for preparation of baked products or low-fructan vegetables.

According to a further aspect of the present invention, there is provided a premix for baking, comprising an enzyme or an enzyme preparation according to the invention, together with one or more ingredients needed or suitable for baking.

A still further aspect of the invention is an improver for baking, comprising an enzyme or enzyme preparation according to the invention, together with one or more ingredients from the group consisting of enzymes, wheat gluten, carriers (wheat gluten maltodextrin etc.), emulsifiers, such as but not limited to DATEM, and mono and diglycerides.

DETAILED DESCRIPTION OF THE INVENTION

Figure 1:
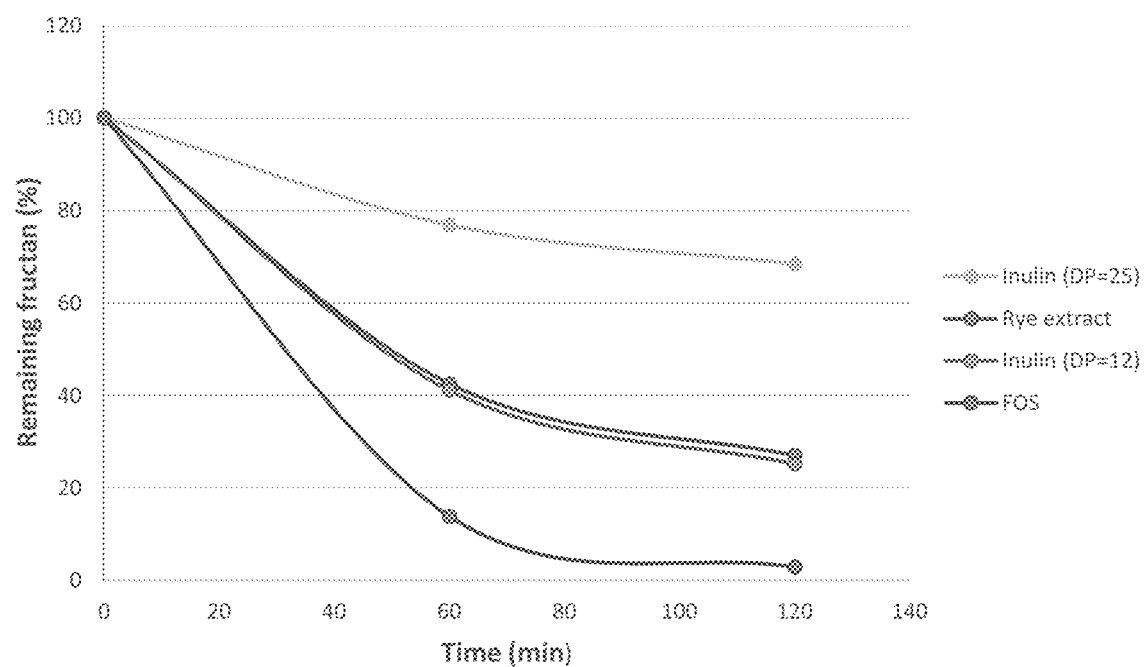
FIG. 1 shows the percentage of residual fructan when the ability of the enzyme to degrade two inulins of different length, FOS compounds and rye meal extract was studied as a function of time. In all reactions the enzyme:substrate ratio was about 2.

In the present context, the term "analogous" used to define the DNA construct of the invention is understood to include any DNA sequence which encodes an enzyme with fructanase activity and which is at least 96% homologous or has at least 96% identity to the DNA sequence shown in SEQ ID No. 1. The analogous DNA sequence may, e.g. be isolated from another organism or may be one prepared on the basis of the DNA sequence shown in SEQ ID No. 1, such as by introduction of nucleotide substitutions which do not give rise to another amino acid sequence of the enzyme. Other examples of possible modifications are insertion of one or more nucleotides into the sequence, addition of one or more nucleotides at either end of the sequence, or deletion of one or more nucleotides at either end or within the sequence.

The present invention provides a novel enzyme that is able to efficiently degrade fructans. The enzyme was isolated and identified from a strain of Lactobacillus having fructan degrading activity. More specifically, the novel extracellular fructanase producing strain was identified as Lactobacillus crispatus. A sample of this microorganism was deposited at the Deutsche Sammlung von Microorganismen and Zellkulturen GmbH (DSM) under accession number DSM 29598.

Lactobacillus strains having fructan degrading activity were isolated from a seed starter generated by back slopping. The seed starter was prepared from grain material having a low content of damaged starch as disclosed in co-pending application PCT/FI2016/050011.

In brief, a seed starter was produced by utilizing back slopping. Back slopping means that small quantities of dough from the manufacture of a fermented product from a previous batch are used as the inoculum or starter for the subsequent batch production. In the preparation of the seed starter, grain material having a low content, preferably less than 1.0% (on grain basis), of damaged starch was used. Grain material was soaked in liquid, preferably water, and incubated at 20-50° C. for 4 to 72 hours. Next day, a fresh batch of the grain material and liquid, preferably water, was mixed as above and inoculated with 1-10% of the previously incubated mixture. This back slopping is carried out several times, preferably at least 3-6 times, and can be continued as long as necessary.

The outcome of the back slopping started from grain material having a low content of damaged starch was the formation of spontaneous microflora that contain microbes that are able to efficiently utilize fructans as a carbohydrate source and quantitatively to consume (and thereby remove) fructans from grain raw material. The adapted microflora had the ability to hydrolyze fructan and further use the possible degradation products and metabolites (fructose, FOS, mannitol) for growth. The flora may also have transport system for fructans or their hydrolysis products or metabolites.

From the seed starter prepared as above, bacterial colonies with different morphology (outlook) were isolated to pure cultures. The microbes of the colonies were analyzed for their efficiency in removing fructan from grain material by using them as pure culture inoculants in laboratory fermentations.

One isolate effective in fructan removal was sequenced and identified as Lactobacillus crispatus (DSM 29598). A novel enzyme of the invention, an extracellular fructosidase and a member of glycosyl hydrolase family 32, was isolated and identified from said strain. It is expected that a DNA sequence coding for a homologous enzyme, i.e. an analogous DNA sequence, may be derived similarly by screening a strain of another microorganism, preferably a Lactobacillus, isolated from a seed starter prepared as described above. Examples of such Lactobacillus strains include but are not limited to other strains of Lactobacillus crispatus, as well as strains of Lactobacillus helveticus, Lactobacillus amylovorus, Lacto bacillus ultunensis, Lactobacillus amylolyticus, Lactobacillus amylovorans, Lactobacillus sobrius or Lactobacillus acidophilus.

The enzyme protein isolated from Lactobacillus crispatus was found to be 95% identical to corresponding proteins in another Lactobacillus crispatus, and 94% and 93% identical to corresponding proteins in L. amylovorus. None of these Lactobacillus enzymes are biochemically characterized. A fructan hydrolase in L. paracasei was previously characterized (Goh et al 2007) but is not homologous to the fructan hydrolase of the L. crispatus described here. The protein has a predicted sec-dependent signal peptide (VKA-DT) and is an extracellular protein.

The novel enzyme of the invention operates over a wide temperature range and shows relatively high activity between 30-60° C. Optimum temperature for fructan hydrolysis is around 50° C. (100% activity) whereas at 30° C. and 60° C. the activity is 80%. The enzyme shows 60% activity at 65° C. and 50% activity at 20° C. The enzyme operates actively in pH range 4-6. It shows maximum activity at pH 5.0 and very high activity (>95%) at pH-values 4.5 and 5.5. At pH-values 4.0 and 6.0 the activity is 75-80% of the maximum.

The above mentioned properties show that the enzyme of the present invention is stable and active over a wide temperature and pH range. Said properties make the enzyme of the present invention particularly suitable for use in the preparation of low-fructan grain and vegetable materials as well as low-fructan grain and vegetable ingredients and products that are suitable for example for a low-FODMAP diet.

The DNA construct of the invention is understood to include any DNA sequence which encodes an enzyme with fructanase activity and which has at least 96%, preferably at least 97%, even more preferably at least 98%, and still more preferably at least 99% identity to the DNA sequence shown in SEQ ID No. 1. Thus, the invention is intended to include any changes in the fructanase coding region which either lead to the same amino acid sequence or to an amino acid sequence which, notwithstanding one or more deviations from the original amino acid sequence, corresponds to an enzyme having essentially fructanase activity.

A further aspect of the present invention provides a recombinant expression vector comprising a DNA construct as defined above. A still further aspect is a host cell transformed with a recombinant expression vector as defined above. The host cell may be for example a bacterium, such as a strain of *Escherichia coli*, or a yeast, such as *Pichia pastoris*.

The invention covers the enzyme irrespective of how it has been produced, for example by recombinant DNA technology, chemical synthesis, enzymatic degradation or a combination thereof. Further, the invention not only covers the enzyme as such, but also in the form of a fusion protein or as a protein physically or chemically bound to any substance and having fructanase activity.

Another aspect of the invention is a method of producing an enzyme exhibiting fructanase activity, comprising the expression in a suitable host of a DNA as defined herein which encodes a fructanase enzyme. As stated above, the expression may take place in various host cells, among which *Pichia pastoris* is preferred. The invention also includes a method as defined above wherein the fructanase enzyme produced is recovered from the culture medium.

An object of the invention is also an enzyme preparation or an improver comprising an enzyme according to the invention, together with carriers and/or emulsifiers. Carriers may include for example wheat gluten, maltodextrin etc. Suitable emulsifiers include emulsifiers known to a person skilled in the art, such as for example DATEM.

The enzyme preparation may be prepared in accordance with the methods known in the art and may be in the form of a liquid or a dry preparation. For instance, the enzyme preparation may be in the form of a granulate or a microgranulate. The enzyme to be included in the preparation may be stabilized in accordance with methods known in the art.

In addition to the enzyme according to the invention, the enzyme preparation may also comprise one or more enzymes having hydrolase activity. The enzymes having hydrolase activity may liberate for example glucose or maltose. Such enzymes include for example α-glucosidase (liberating glucose from starch/maltodextrin), β-glucosidase (liberating glucose from β-glucan), invertase (liberating glucose from sucrose), and amylolytic enzymes (liberating maltose from starch). A benefit of having glucose and fructose present in the product formulation is that fructose absorption from small intestine is improved when glucose is present in equal or higher amounts compared with fructose. Another benefit is to gain balanced taste of sweetness; although fructose is sweeter than glucose or maltose or sucrose, its combination with glucose, for instance, creates sweetness that is perceived more complete in its profile of sweet taste. The liberation of sugars (glucose, fructose, maltose) from raw materials or ingredients during food processing, thus, increases "natural" sweetness and, thereby, reduces the need to include added sugar in the product formulations.

The novel enzyme and the novel enzyme preparation according to the invention can be used in the degradation of fructan of grain materials or vegetables. Suitable grain materials include, without limitation, wheat, rye, barley, and mixtures thereof. A mixture may comprise all three of the mentioned grain materials or a combination of any two of them. Suitable vegetable materials include all vegetables that contain fructan (e.g. inulin). Examples of such vegetables include onions, garlic, Jerusalem artichoke, chicory root etc.

The dosage of the novel enzyme and the novel enzyme preparation needed to degrade fructan in a certain material depends on the activity of enzyme, the amount of fructan in the material and the conditions under which the enzyme or the preparation is used and may be determined on the basis of methods known in the art. For example, at an activity level of approximately 500 U/g, an enzyme/substrate ratio of in the range of 2:1 to 3:1, preferably about 2.5:1, may be used. In baking, the amount of enzyme needed naturally depends on the amount of fructan in the flours used. In the case of wheat, 0.1% enzyme based on the weight of wheat flour may be sufficient. In the case of rye, the amount of the enzyme is preferably over 0.5%, based on the weight of rye flour.

The novel enzyme can thus be used in the preparation of baked products, wherein it has been found to effectively reduce the content of fructan. In laboratory, FOS compounds were almost totally degraded by the enzyme. In rye extract, over 70 or 80% of the fructan of rye extract was degraded by the novel enzyme.

When used in baking, the novel enzyme reduced the fructan conten of rye and wheat doughs to almost zero at the end of rising the dough. At the same time, the amount of fructose increased compared to a control dough without the enzyme.

The novel enzyme can also be used in the preparation low-fructan vegetables wherein it has been found to degrade approximately 60% or more of the original fructan content of vegetables.

With the novel enzyme or the novel enzyme preparation it is thus possible to provide wheat, rye, barley and vegetable materials and products that are substantially free from fructan and thereby are suitable for a specific diet such as low-FODMAP diet.

A further object of the invention is a premix for baking comprising the novel enzyme according to the invention or the enzyme preparation according to the invention. Without limitation, premixes typically include whole, crushed or milled wheat, other cereals, pulses, nuts and seeds, but also carriers, fibers and water binders such as, but not limited to, maltodextrins, celluloses, pectins, protein concentrates (gluten etc). Premixes may or may not include bread/dough improvers and/or their constituents.

A still further aspect of the invention is an improver for baking, comprising an enzyme or enzyme preparation according to the invention, together with one or more ingredients from the group consisting of enzymes, wheat gluten, carriers (wheat gluten maltodextrin etc.), emulsifiers such as but not limited to DATEM, and mono and diglycerides.

The enzyme may also be used to liberate fructose from fructan. It can be used together with other enzymes, for instance hydrolases that liberate glucose or maltose from sucrose, glucans as starch or beta-glucan or maltodextrin. Enzymes that can release glucose from described substrates include invertases, amylolytic enzymes, alpha-glucosidases and beta-glucosidases. Release of fructose and/or glucose enables to decrease the amount of added sugar needed to provide the desired sweetness to the product in question.

At least some embodiments of the present invention find industrial application in food industry, in particular in baking products and in preparation of low FODMAP vegetables. In addition, specific liberation of fructose finds industrial application in food industry as well.

The enzyme of the invention can obviously also be applied outside food industry. For instance, the enzyme can be used in biofuel production to liberate fructose from materials containing fructan or in feed production to pretreat animal foods to decrease the amount of fructan and thereby to improve the digestion and nutritional value of feed. For instance, horses may suffer from laminitis, which is proposed to be the cause of feed containing grains or grass high in non-absorbable carbohydrates e.g. fructan. This leads to excess gut fermentations which are believed to cause the condition. The enzyme can also be applied as a digestive-aid enzyme in nutraceutical products similarly as lactase enzyme is added to improve lactose digestion. The enzyme could also be used in dental care to decrease the amount of plaque. It is known that fructans play a role in the formation of dental plaque biofilm and that the use of fructanase could reduce the amount of plaque.

While the following examples are illustrative of the principles of the present invention in one or more particular application, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also unrecited features. The features recited in depending claims are mutually freely combinable unless otherwise explicitly stated.

Furthermore, it is to be understood that the use of "a" of "an", that is, a singular form, throughout this document does not exclude a plurality.

EXPERIMENTAL

Example 1. Production of a Seed Starter and Isolation of Pure Cultures

A seed starter was produced from cut kernels of rye without a pre-existing seed starter. The cut kernels used in the example contain 0.2% of damaged starch.

100 g of cut kernels were soaked in 150 g of water and incubated at 45° C. After 24 h 10 g of the above mixture was mixed with 100 g of cut kernels of rye and 150 g of water and incubated at 45° C. for 24 h. This back slopping was repeated five more times.

From the seed starter prepared as above, bacterial colonies with different morphology (outlook) were isolated to pure cultures. The microbes of the colonies were analyzed for their efficiency in removing fructan from grain material by using them as pure culture inoculants in laboratory fermentations. In each fermentation reaction, 20 g of cut grains of rye were mixed with 30 grams of tap water and 500 mg pure culture starter suspension containing $10^9$ cells of microbe isolate. After 16 hours fermentation at 37° C., the fructan content of the mixtures were analyzed using a commercial kit (K-FRUC, Megazyme). The initial fructan content of the grain material was 5% (on a dry matter basis).

One isolate effective in fructan removal was identified as *Lactobacillus crispatus*.

Example 2. Identification of Fructan Hydrolase from L. *Crispatus* (DSM 29598)

Genomic DNA Isolation and Sequencing:

Genomic DNA was isolated using the Wizard® Genomic DNA Purification Kit (Promega) following the manufacturer's guidelines. The quality and quantity of each sample was assessed using gel electrophoresis and a NanoDrop Spectrophotometer. Samples were sent to Axeq Technologies (Seoul, South Korea) where they underwent further quality checks and genomic sequencing.

Whole-Genome Sequencing, Assembly and Annotation:

The samples were sequenced using Illumina HiSeq2000 with >500 fold coverage and the quality of the paired-end reads was assessed using the FastQC tool provided in a Galaxy software bundle. Reads were assembled de novo using ABySS (Assembly By Short Sequence; into contigs using a kmer value of 63. Repetitive sequences and short assemblies were removed by filtering out contigs <500 bp in size. The sequence result was 103 contigs.

The evolutionary history was inferred by using the Maximum Likelihood method based on the JTT matrix-based model. The tree is drawn to scale, with branch lengths measured in the number of substitutions per site. Evolutionary analyses were conducted in MEGA6.

As a result, an extracellular fructosidase, a member of glycosyl hydrolase family 32 was identified. The enzyme protein is >93% identical to corresponding proteins in *L. amylovorus*, 56% identical to the fructan hydrolase in *Atobobium parvulum* and >55% identical to fructan hydrolases in *S. mutans*. The protein has a predicted sec-dependent signal peptide (VKA-DT) and is thus likely an extracellular protein. The phylogenetic analysis showed that there are few homologues in *Lactobacillus* spp., none of these are biochemically characterized. The fructan hydrolase in *L. paracasei* that was previously characterized is not homologous to the fructan hydrolase of the presently studied *L. crispatus*.

Example 3. Production of Enzyme

The enzyme was produced in *Pichia pastoris*, a methylotrophic yeast that is widely used in the extracellular expression of recombinant proteins, by following routine recombinant DNA procedures. Standard methods in the enzyme production were performed essentially as described in Maniatis 1989, Molecular Cloning, CSH, N.Y., USA.

Example 4. Enzyme Reactions

Fructan Degradation

Fructan degradation ability of the enzyme was examined by two inulins of different length (inulin HP (DPav=25) and inulin GR (DPav=12)), by FOS compounds and by rye meal extract. For the enzyme reaction, an enzyme solution was prepared, having a concentration of 10 mg/ml, and a substrate solution, having a concentration of 4 mg/ml. For the manufacture of both solutions, 0.1 M sodium acetate buffer (pH 4.5) was used. 0.5 ml of each solution was transferred to the reaction mixture. When rye extract was used as a substrate, the concentrations were half the size. The enzyme reaction was carried out at 50° C. and the reaction time was 2 hours. Samples were taken after 60 min and after 120 min. A solution wherein the enzyme solution was replaced by 0.5 ml of 0.1 M sodium acetate buffer (pH 4.5) was used as a standard. Reactions were stopped by placing the samples for 5 min in a boiling water bath, and then they were allowed to stand for 5 min in a cold water bath. Prior to the determination of fructan concentrations, the samples were allowed to stand for about 10 min at room temperature. They were diluted with deionized water so that the maximum fructan concentration was 1 mg/ml. The amount of fructan degradation by the enzyme was obtained by subtracting the amount of fructan in the reaction mixture from the amount of fructan in the standard.

In the reactions an enzyme compound was used, which had declared activity of 516.6 U/g. The enzyme/substrate ratio in the reactions was about 2. FIG. 1 shows the percentage of remaining residual fructan based on the initial concentration. The diagram shows that the FOS compounds are mostly degraded by the enzyme, while longer chain inulin is less degraded. After two hours, 68.5% of the longer inulin was remaining whereas there were only 3.0% of FOS compounds. The shorter inulin and rye extract were about equally broken down in percentage terms (inulin 25.3% and rye extract 27.1% fructan left).

Figure 2:
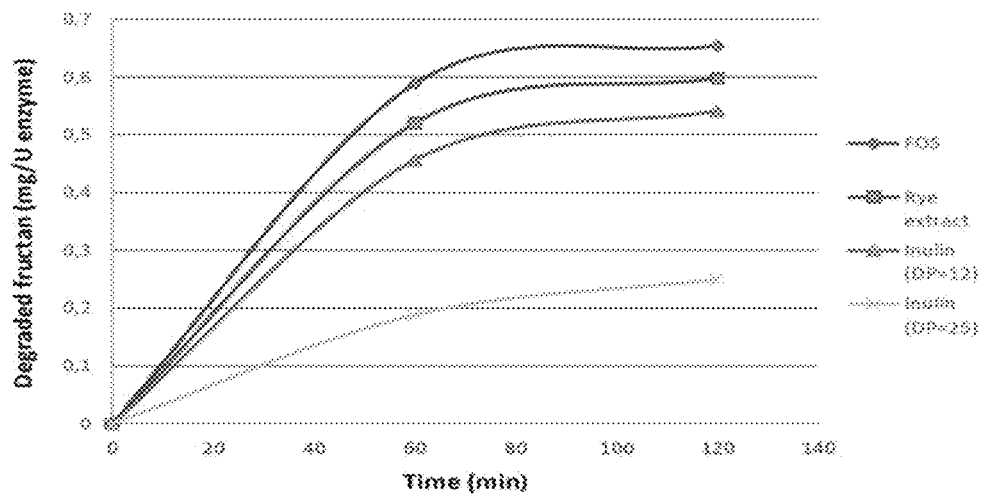
FIG. 2 shows the amount of substrate degraded by the enzyme per enzyme activity unit.

Since the enzyme/substrate ratios varied slightly for each substrate, the amount of substrate degraded by the enzyme was calculated also per enzyme activity unit (FIG. 2). The highest degradation was found with FOS compounds, while the shorter inulin had the lowest degradation. During two hours, FOS compounds had a degradation rate of 0.654 mg/U, whereas that of inulin was 0.25 mg/U. Fructan of rye extract had a better degradation rate relative to the amount of enzyme than the shorter inulin (rye 0.598 mg/U and inulin 0.541 mg/U).

Both diagrams show that the enzyme decomposes substrates at a higher rate during the first hour and thereafter the degradation rate decreases.

Fructose Formation

Figure 3:
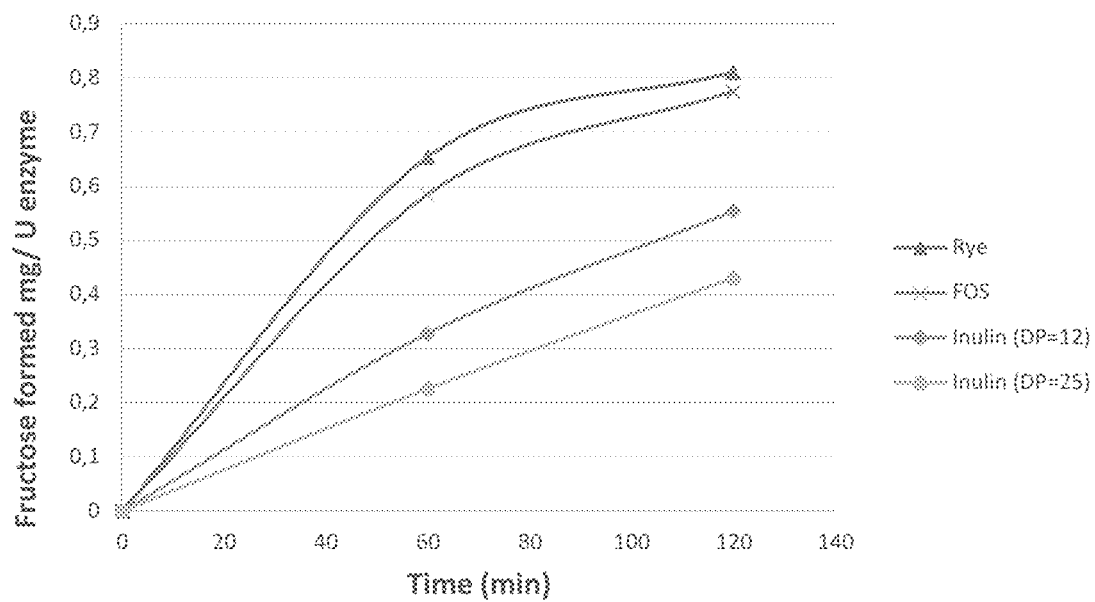
FIG. 3 illustrates the amount of fructose formed.

In addition to fructan concentrations, also fructose concentrations in the reactions were measured after 60 min and 120 min reaction times. FIG. 3 shows the increase in fructose concentrations as a function of time. The resulting fructose is shown per enzyme activity unit. The highest amounts of fructose were formed with rye extract and FOS compounds as substrates. From the shorter inulin 0.775 mg U fructose was formed in two hours. The lowest amount of fructose was formed when the longer inulin was the substrate (0.431 mg/U). When rye extract and FOS compounds were used as substrates, the formation of fructose was significantly lower after an hour. Fructose formation from inulin was almost at the same level during the two hours. The samples were also assayed for glucose and sucrose content, but those compounds were almost not formed in the reactions.

Degrees of hydrolysis were calculated on the basis of fructose formation of different substrates. FOS compounds hydrolyzed almost completely (96.6%), which was very close to the value obtained from fructan assays. Also, degrees of hydrolysis of the shorter inulin and rye extract were very close to the estimated degradation rate based on fructan measurements. Instead, longer inulin hydrolyzed considerably more calculated on the basis fructose concentrations, the degree of hydrolysis being 55.0%, based on fructose, and 31.5%, based on fructan.

TABLE 8

Calculated degrees of hydrolysis based on fructose formation for various substrates after a reaction time of two hours

| Substrate | Degree of hydrolysis (%) |
| --- | --- |
| FOS | 96.6 |
| Inulin (DPav = 10) | 75.5 |
| Inulin (DPav = 23) | 55.0 |
| Rye extract | 81.3 |

Figure 4:
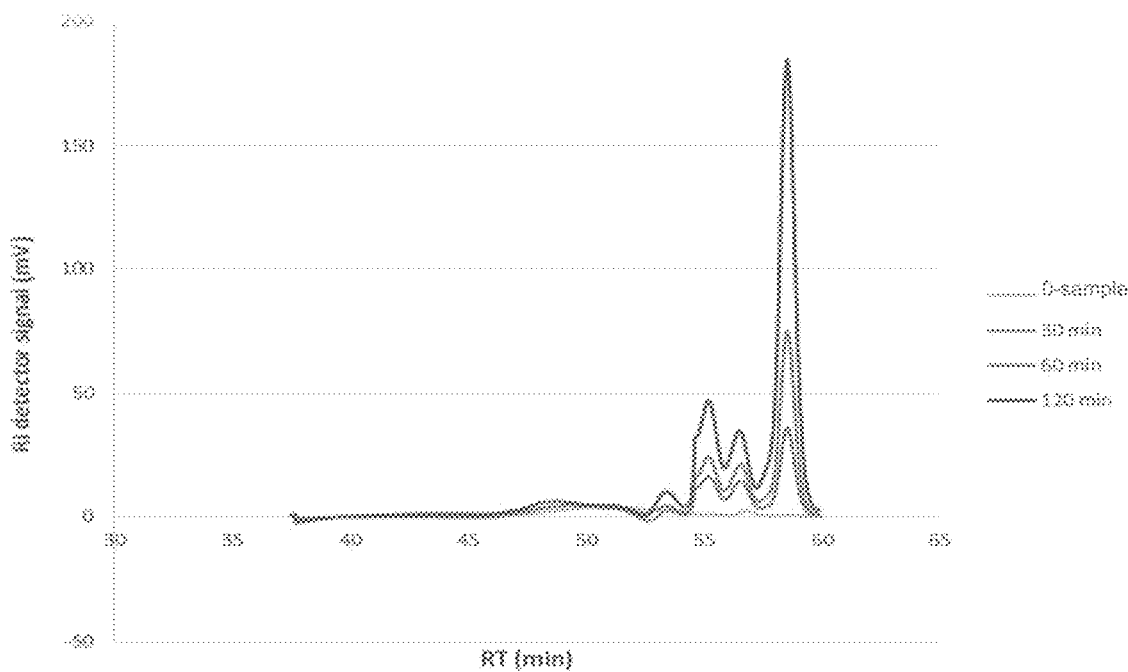
FIG. 4 shows the results of gel filtration chromatography for inulin (DPav=12) and its degradation products. Samples were taken after a reaction time of 30 min, 60 min and 120 min. In all samples, the background signal caused by the enzyme has been reducted.

Hydrolysis method Gel filtration chromatography was used to clarify whether the enzyme first degrades its substrate into FOS compounds or whether it releases single fructose molecules from the ends of fructan chain. Measurements were made for inulin reactions and the degradation products were determined for samples taken at 30 min, 60 min and 120 min. In addition, blank samples containing only the substrate were determined. FIG. 4 shows the spike formed by the shorter inulin and its degradation products. The low peak at about 50 minutes represents inulin and the other peaks represent degradation products. The highest peak on the graph shows the fructose, and FOS compounds are also formed in the reaction. Based on the molecular weights, FOS compounds have about 2 to 3 fructose units.

Figure 5:
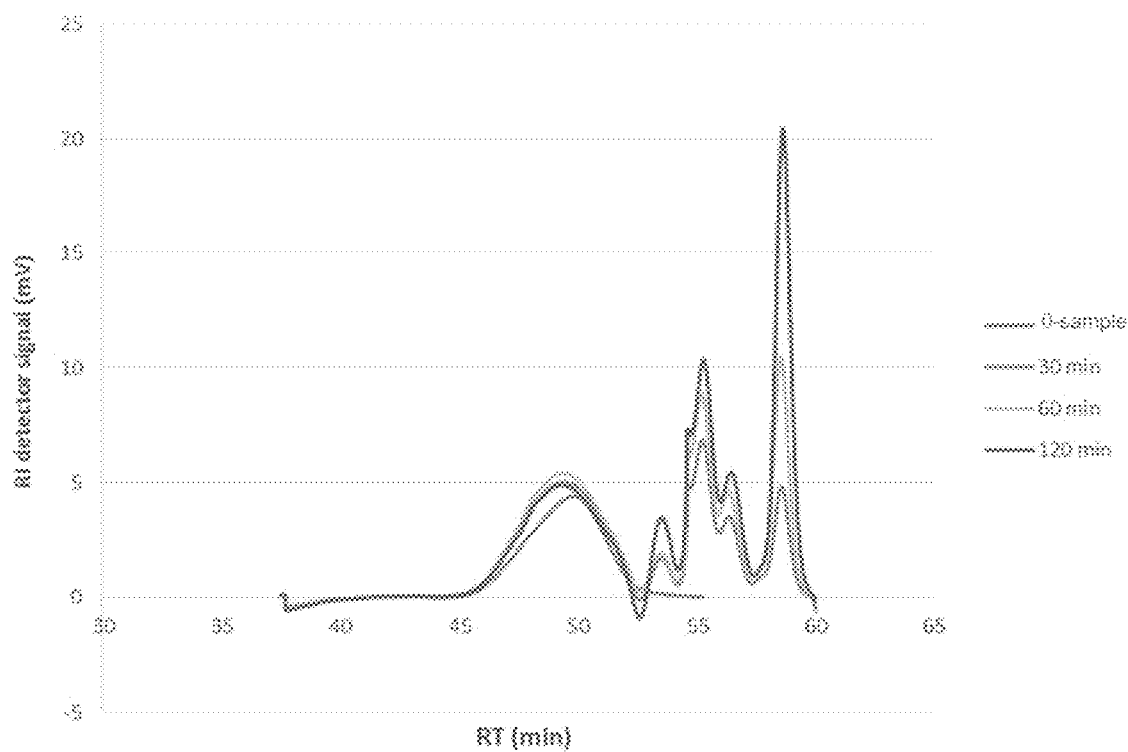
FIG. 5 shows the results of gel filtration chromatography for inulin (DPav=25) and its degradation products. Samples were taken after a reaction time of 30 min, 60 min and 120 min. In all samples, the background signal caused by the enzyme has been reducted.

FIG. 5 shows the peak formed by the longer inulin and its degradation products. The reaction forms the same end products as the reaction of the shorter inulin. However, at the site of FOS compounds there are more of those FOS compounds that are three units long than those that are two units long. Moreover, the graph clearly shows that there is plenty of inulin left even after two hours.

Example 5. Baking

The ability of the enzyme to degrade fructan in a baking process was studied by adding enzyme to wheat and rye doughs. Table 1 shows the basic recipe of wheat and rye doughs. The amount of enzyme in the wheat dough was 0.175%, based on the weight of wheat flour, and in rye dough 0.68%, based on the weight of rye flour. The flour in the starter culture is not taken into account in the calculation. In addition to enzyme doughs/breads, control doughs without added enzyme were prepared.

TABLE 1

Ingredients of wheat and rye doughs and their amounts based on the amounts of wheat and rye flour

| Ingredient | Wheat dough (%) | Rye dough (%) |
| --- | --- | --- |
| Wheat flour | 100 | — |
| Rye flour | — | 100 |
| Starter culture | — | 74 |
| Water | 67 | 61 |
| Yeast | 3 | 1.2 |
| Salt | 1.7 | 2.3 |
| Sugar | 1.8 | — |
| Oil | 1.2 | — |

The doughs were prepared by mixing all the ingredients. Wheat doughs were stirred for approximately 5 min and rye doughs until the ingredients were mixed. The enzyme was added to water before the other ingredients. The doughs were allowed to rise for two hours at a temperature of 37° C. Samples of the doughs were taken immediately after mixing and after rising of 30 min, 60 min and at the end of the rising. The doughs were baked for 20 min at a temperature of 210° C. The last sample was taken from cooled breads. All the samples were frozen and assayed for fructan and fructose concentrations. Rye dough samples were assayed also for mannitol concentrations.

Fructan Concentrations in Doughs

Figure 6:
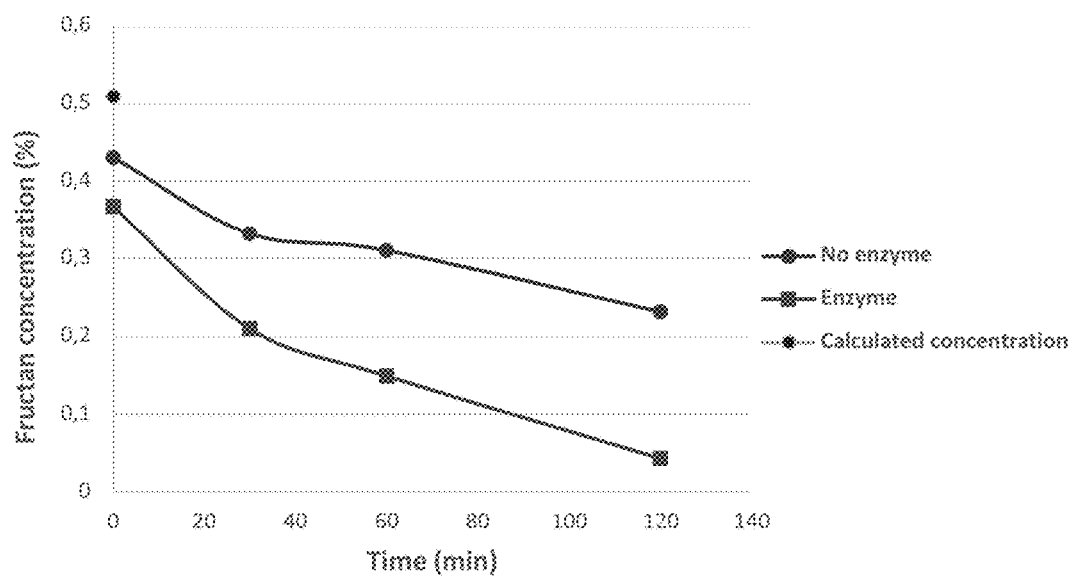
FIG. 6 shows fructan concentrations in wheat doughs during two hours of rising. The figure also shows calculated fructan concentration at the beginning of rising, based on the measured fructan content of wheat flour.

Fructan concentrations in wheat doughs during two hours of rising are shown in FIG. 6. Fructan concentration in the control dough was 0.43% at the beginning of rising and it decreased to 0.23% during two hours. In the dough with added enzyme, the concentration was 0.37% at the beginning of rising and 0.04% at the end of rising. In both doughs, the fructan concentrations were lower than was expected based on the fructan concentration of wheat flour.

Figure 7:
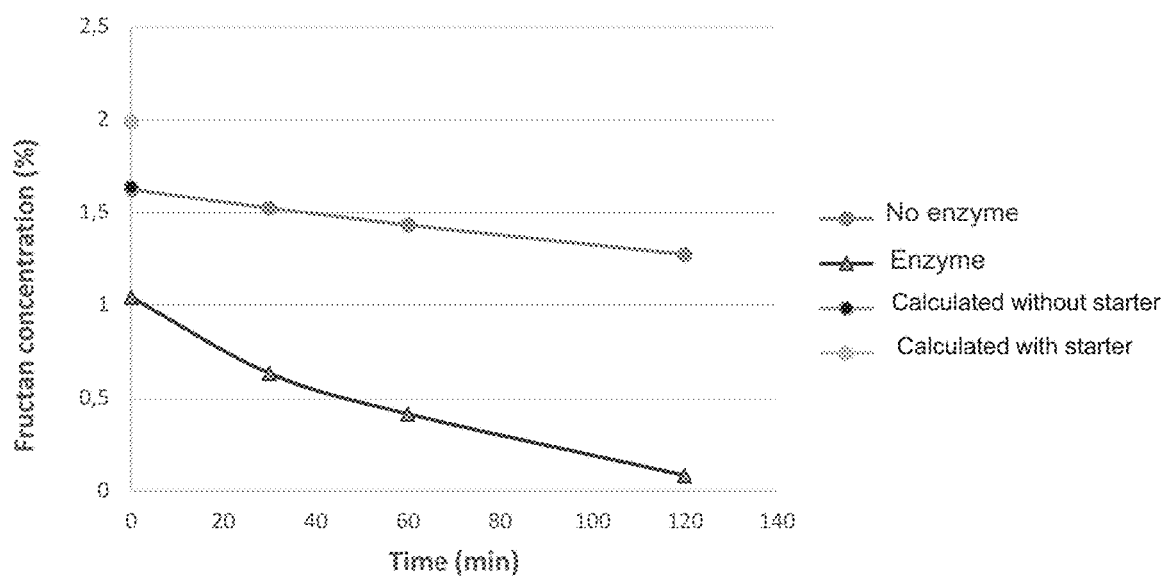
FIG. 7 illustrates the change in fructan concentrations of rye doughs during two hours of rising. The figure also shows theoretical fructan concentration at the beginning of rising, with and without taking the fructan of the starter culture into account.

FIG. 7 shows the change in fructan concentrations of rye doughs during two hours of rising. FIG. 7 also shows theoretical fructan concentrations at the beginning of rising, with and without taking the fructan of the starter culture into account. Fructan concentration in the control dough was 1.6% at the beginning of rising and 1.3% at the end of rising. In the dough with added enzyme, the concentrations were 1.0% at the beginning and 0.08% at the end. The diagram also shows how the fructan content of the enzyme dough is remarkably smaller than that of the control already at the beginning of rising.

Fructose Concentrations in Doughs

Figure 8:
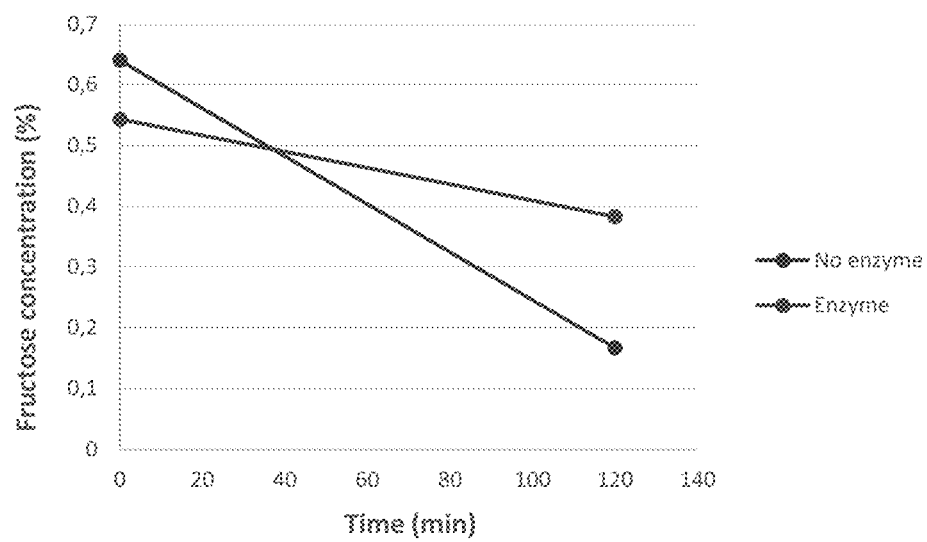
FIG. 8 illustrates fructose concentrations in wheat doughs at the beginning and at the end of rising.

Fructose concentrations in the doughs were determined at the beginning and at the end of rising. FIG. 8 shows the changes in fructose concentrations of the wheat doughs after two hours. Surprisingly, the fructose content of the control dough (0.64%) at the beginning of rising was higher than that of the enzyme dough (0.54%). During two hours, however, the control dough concentration decreased considerably more than that of the enzyme dough, the concentrations being 0.17% in the control dough and 0.38% in the enzyme dough.

Figure 9:
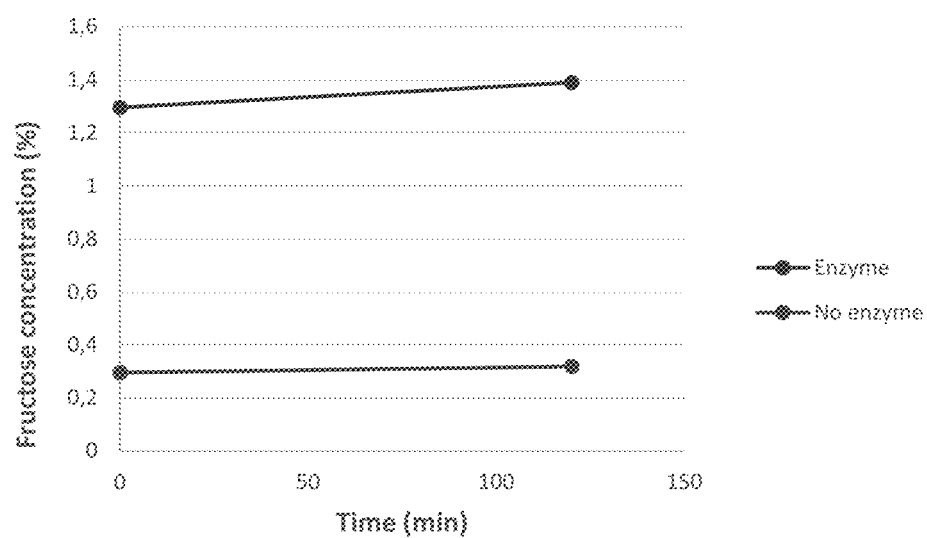
FIG. 9 illustrates fructose concentrations in rye doughs at the beginning and at the end of rising.
Figure 10:
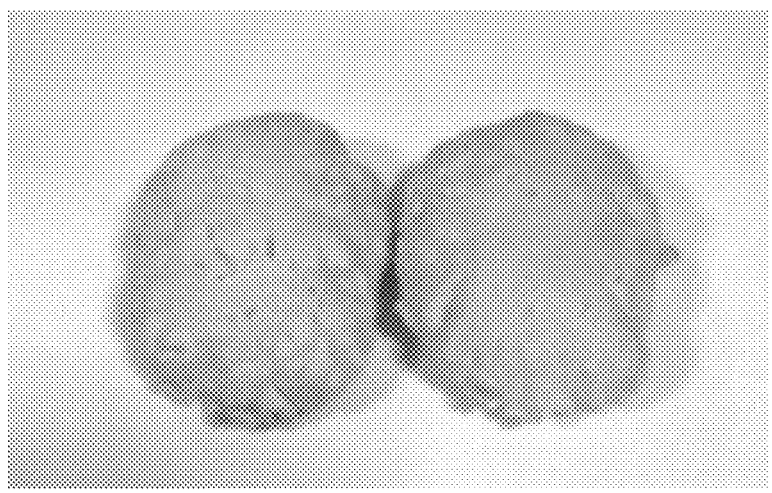
FIG. 10 shows the outlook of baked bread with and without enzyme addition. Control bread on the left, enzyme bread on the right.

In rye doughs, the fructose concentrations remained also the same when concentrations at the beginning and at the end of rising were compared (FIG. 9). The fructose concentrations of the control dough were 0.30% at the beginning and 0.32% at the end of rising. In the enzyme dough, fructose concentration was 1.29% at the beginning and 1.39% at the end of rising.

Baked Bread

Finally, the doughs were baked and fructan and fructose concentrations of the final baked breads were determined. Mannitol concentrations of rye bread were also determined. Mannitol assay was made by D-mannitol/L-arabitol Assay Kit method. 1-2 g samples were weighed and then they were dissolved in water by heating and stirring. The assay was made according to the instructions of the manufacturer. In the treatment of solid samples, the samples were not filtered after dissolving in water but centrifuged for 5 minutes (5000 rpm).

The results are summarized in Table 2. Overall, the levels increased slightly during cooking (water evaporation). Fructan content of wheat bread containing enzyme was 0.05%. Fructan content of rye bread containing enzyme was 0.15%. Mannitol concentrations of the rye breads were very similar to each other. In particular, rye bread with enzyme contained more fructose than the control.

TABLE 2

Fructan, fructose and mannitol concentrations of baked breads

| Bread | Fructan (%) | Fructose (%) | Mannitol (%) |
|---|---|---|---|
| Wheat, control | 0.25 | 0.01 | — |
| Wheat, enzyme | 0.05 | 0.40 | — |
| Rye, control | 1.40 | 0.20 | 0.34 |
| Rye, enzyme | 0.15 | 1.31 | 0.36 |

Figure 11:
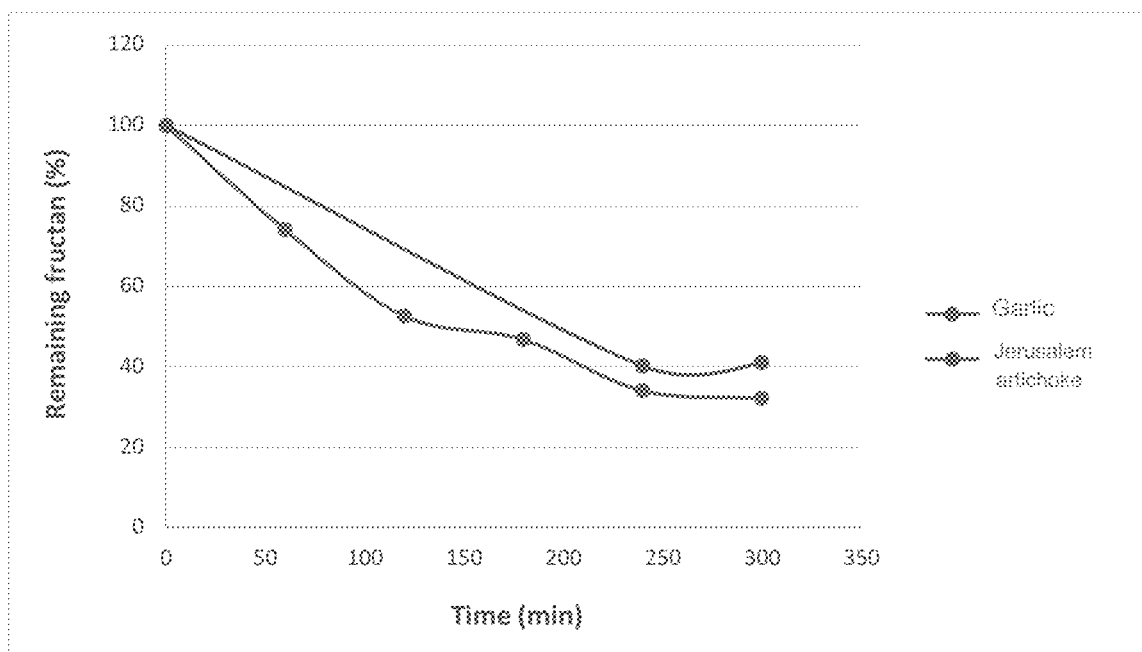
FIG. 11 shows the percentage of residual fructan when the ability of the enzyme to degrade garlic and Jerusalem artichoke was studied as a function of time.

Baked wheat and rye breads were also sensory evaluated. Evaluated properties included crust color, texture and softness of the bread, as well as shelf life. The breads were also weighed and measured for volume. There was hardly any difference in the enzyme breads compared to the control breads. The only difference detected was the crust colour of wheat breads. The crust of the enzyme bread was slightly darker than that of the control (FIG. 11).

Example 6. Vegetable Treatment a) Garlic

Garlic contained around 20 g fructan/100 g (fresh weight). Four grams of garlic was crushed and mixed with 50 mL of tap water. The fructanase enzyme (1000 U) was added and the suspension was incubated at 50° C. for 5 hours. Samples were analysed at time points of 0 h, 4 h, and 5 h. The fructan content decreased during 4-5 hours of incubation leaving the residual fructan content 40% of the 0 h sample (FIG. 11).

b) Jerusalem Artichoke

Jerusalem artichoke contained around 12% fructan/100 g (fresh weight). Eight grams of Jerusalem artichoke was sliced cut into small pieces and mixed with 30 mL of tap water. The fructanase enzyme (1250 U) was added and the mixture was incubated at 50° C. for 5 hours. Samples were analysed at time points 0 h, 1 h, 2 h, 3 h, 4 h, and 5 h. The fructan content decreased steadily leaving 32% of residual fructan after 5 h of incubation (FIG. 11).

Example 7. Baking (Mixture of Flours)

The enzyme was tested in a straight dough baking process for mix-bread containing a mixture of wheat, oats and rye flours. Ingredients (see Table 3) were mixed for 5 min in a dough mixer and the dough was allowed to rest for 20 min.

TABLE 3

Ingredients of mix-bread containing wheat, oats and rye flours (g)

| Ingredient | Blanco | Enzyme |
|---|---|---|
| Water | 2.000 | 2.000 |
| Wheat flour | 0.800 | 0.800 |
| Oat flour | 0.800 | 0.800 |
| Rye flour | 0.500 | 0.500 |
| Salt | 0.050 | 0.050 |
| Oil | 0.100 | 0.100 |
| Dry yeast | 0.020 | 0.020 |
| Enzyme | 0 | 0.004 |

The dough was moulded to flat breads that were proofed for 45 min at 40° C. and oven-baked at 230° C. for 15 min and cooled down at room temperature. The fructan content was determined after cooling. The fructan contents were 0.34% for Blanco-bread and 0.17% for Enzyme-bread.

CITATION LIST

Patent Literature

EP 1084624 A2
US 20110129572 A1
WO 2010/097416 A1

Non Patent Literature

Andersson, R., Fransson, G., Tietjen, M. & Aman, P. (2009). Content and molecular-weight distribution of dietary fiber components in whole-grain rye flour and bread. *Journal of Agricultural and Food Chemistry* 57 (5), 2004-2008.

Goh Y J., Lee J H & Hutkins R W. (2007) Functional Analysis of the Fructooligosaccharide Utilization Operon in *Lactobacillus paracasei* 1195. *Appl. Environ. Microbiol.* 73 (18) 5716-5724.

Müller, M. and Lier, D. (1994). Fermentation of fructans by epiphytic lactic acid bacteria. *Journal of Applied Bacteriology* 76 (4), 406-411.

Müller, M. and Seyfarth, W. (1997). Purification and substrate specificity of an extracellular fructanhydrolase from *Lactobacillus paracasei* ssp. *paracasei* P 4134. *New Phytol.* 136, 89-96.

Paludan-Müller, C., Gram L. & Rattray, F. P. (2002). Purification and Characterisation of an Extracellular Fructan β-fructosidase from a *Lactobacillus pentosus* Strain isolated from Fermented Fish. *System. Appl. Microbiol.* 25, 13-20.

Rakha A., Åman, P. & Andersson, R. (2010). Characterisation of dietary fibre components in rye products. *Food Chemistry* 119 (3), 859-867.

---

The invention claimed is:

1. A method for improving the digestibility or nutritional value of a fructan-containing animal feed for an animal, the method comprising pre-treating the animal feed with the enzyme of SEQ ID NO: 2 prior to delivery of the animal feed to the animal.

2. The method of claim 1, wherein the animal feed is horse feed.

3. The method of claim 1, wherein the animal feed comprises a grain material or a grass material comprising fructan.

4. A method for treating laminitis in a horse comprising delivering to the horse an amount of the enzyme of SEQ ID NO: 2.

5. A method for improving digestion in a subject comprising delivering a nutraceutical product to the subject, the nutraceutical product comprising the enzyme of SEQ ID NO: 2 having fructan hydrolase activity.

6. A method for reducing an amount of fructan in a fructan-containing food product comprising mixing an enzyme comprising the sequence of SEQ ID No. 2 having fructan hydrolase activity with the food product.

7. The method of claim 6, wherein the fructan-containing food product is selected from the group consisting of an animal feed, a vegetable material, a grain material, and a dough containing fructan.

8. The method of claim 6, wherein the fructan-containing food product comprises a vegetable material selected from the group consisting of onion, garlic, Jerusalem artichoke, and chicory root.

9. The method of claim 6, wherein the fructan-containing food product comprises a flour selected from the group consisting of a wheat flour, a rye flour, a barley flour, an oat flour, and mixtures thereof.

10. The method of claim 6, wherein the fructan-containing food product comprises a dough selected from the group consisting of a wheat dough, a rye dough, an oat dough, and mixtures thereof.

11. The method of claim 6, wherein the fructan-containing food product further comprises one or more additional enzymes having hydrolase activity.

12. The method of claim 6, wherein the food product further comprises an amount of glucose and fructose, and wherein the glucose is present in a greater amount than the fructose.

13. A method for reducing dental plaque in a subject comprising administering to the subject an amount of the enzyme of SEQ ID NO: 2 having fructan hydrolase activity effective to reduce dental plaque formation.

* * * * *